United States Patent [19]

Iwata et al.

[11] Patent Number: 4,495,149
[45] Date of Patent: Jan. 22, 1985

[54] OPTICAL-TYPE AUTOMATIC ANALYZING AND MEASURING APPARATUS

[75] Inventors: Toyotaro Iwata; Kunio Nakajima; Hiroyuki Otsuki, all of Hyogo, Japan

[73] Assignee: Toa Medical Electronic Co., Ltd., Hyogo, Japan

[21] Appl. No.: 419,038

[22] Filed: Sep. 16, 1982

[30] Foreign Application Priority Data

Sep. 18, 1981 [JP] Japan .................... 56-147165

[51] Int. Cl.³ .................................................. G01N 35/06
[52] U.S. Cl. .................................... 422/65; 73/864.11;
  73/864.25; 134/170; 141/130; 356/436;
  356/442; 422/67; 422/100; 422/63; 422/99;
  436/49
[58] Field of Search ................................ 422/63–67,
  422/100, 99; 134/170; 141/1,130; 356/39, 436,
  442; 73/864.11, 864.25; 436/49

[56] References Cited

U.S. PATENT DOCUMENTS

| | | | |
|---|---|---|---|
| 3,143,393 | 8/1964 | Des Hons | 422/65 |
| 3,842,680 | 10/1974 | Vollick et al. | 422/100 |
| 3,994,587 | 11/1976 | Yamamoto et al. | 356/73 |
| 4,076,503 | 2/1978 | Atwood et al. | 422/100 |
| 4,204,767 | 5/1980 | Kata et al. | 356/444 |
| 4,299,796 | 11/1981 | Esch | 422/63 |
| 4,332,472 | 6/1982 | Kata et al. | 356/344 |
| 4,338,279 | 7/1982 | Orimo et al. | 422/64 |

OTHER PUBLICATIONS

Levine et al., Telescoping Spectrophotometer Dip Probe, vol. 18, No. 11, IBM Tech. Bulletin, Apr. 1976.

Primary Examiner—Michael S. Marcus
Attorney, Agent, or Firm—Pearne, Gordon, Sessions, McCoy, Granger & Tilberry

[57] ABSTRACT

Disclosed is an analyzing apparatus for applying samples and reagents to the surface of a reaction carrier and for optically analyzing each component contained in the various samples. The dispensing of the samples and reagents and the optical detection operation are performed by an optics/dispensing mechanism moved relative to the reaction carrier in two dimensions. The optics/dispensing mechanism is combined with a cleaning apparatus for cleansing reagents and samples from a dispensing needle by means of a rinsing agent and air ejected toward the needle. The apparatus further includes an automatic lifting mechanism for lifting and replacing a cover disposed on the reaction carrier, and is adapted to move the dispensing needle to a position over a nearby reagent/sample holder so that the needle may take up a desired reagent or sample from the holder and transfer it to the surface of the reaction carrier. The apparatus is capable of performing highly accurate analytical measurements fully automatically and in continuous fashion.

15 Claims, 37 Drawing Figures

Fig. 23
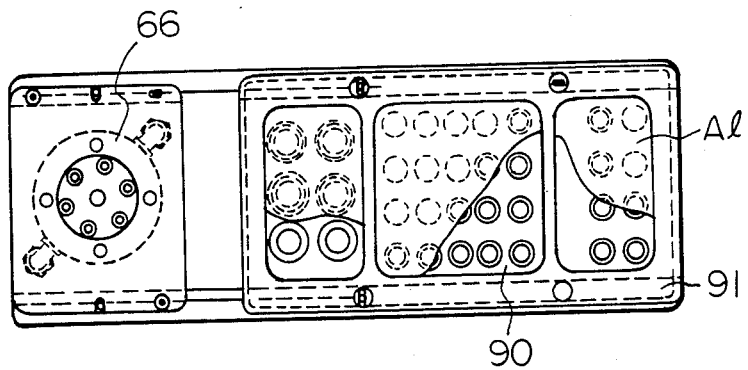
Fig. 24
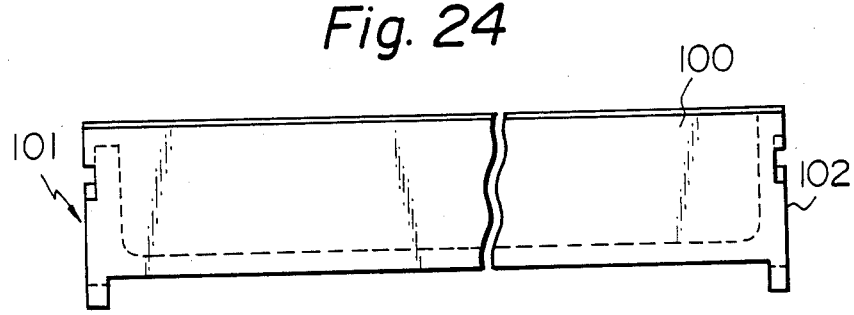
Fig. 25          Fig. 26
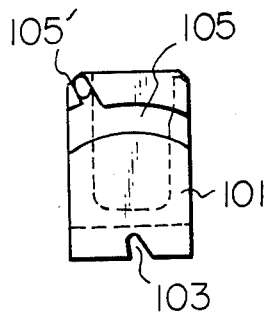  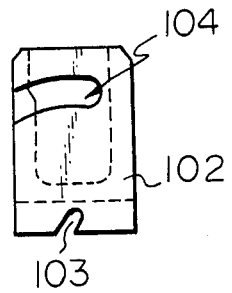

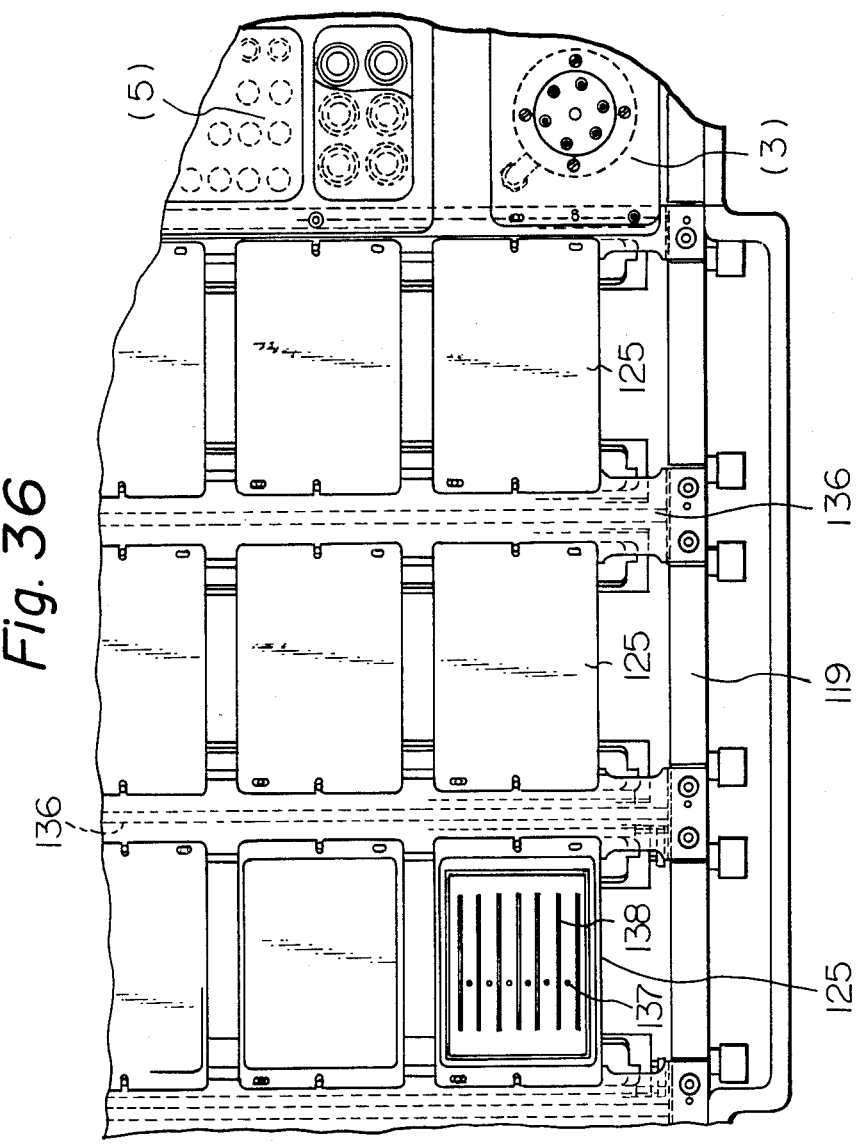

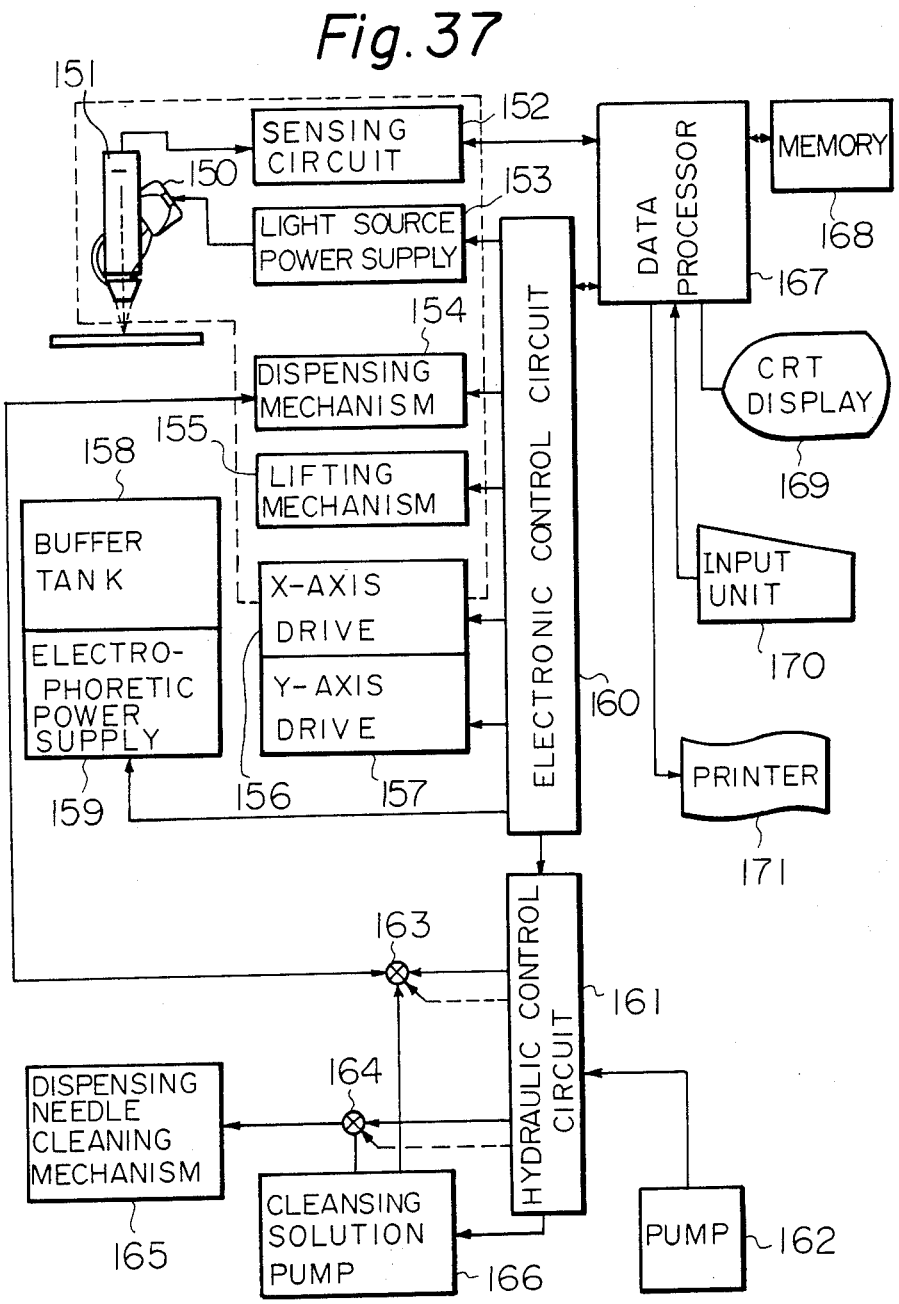

OPTICAL-TYPE AUTOMATIC ANALYZING AND MEASURING APPARATUS

BACKGROUND OF THE INVENTION

This invention relates to an apparatus for dispensing a predetermined trace amount of a sample onto the surface of one or more reaction carriers arrayed in two dimensions, allowing each component contained in the sample to react with a predetermined substance to provide a reaction product of which the coloration or formation of precipitates, etc. is capable of being detected by optical means, and optically scanning the reaction product by optical scanning means to provide a reading of the density or formation pattern for each sample, whereby a qualitative and/or quantitative determination is made with regard to the reaction product.

SUMMARY OF THE INVENTION

An object of the present invention is to provide an optical-type automatic analyzing and measuring apparatus which enables a variety of laboratory and clinical reactions to be analyzed and measured quantitatively and qualitatively absolutely without human intervention through automated dispensing and optical analysis of samples and reagents at predetermined positions in any desired sequence.

Another object of the present invention is to provide an optical-type automatic analyzing and measuring apparatus which is capable of carrying highly accurate measurements based on an electrophoretic method in a fully automated manner.

A further object of the present invention is to provide an optical-type automatic analyzing and measuring method which, through a combination of analytical and electrophoretic means and a fully mechanized dispensing system, is capable of carrying out highly accurate and fully automatic measurements based on immunoelectrophoresis.

According to the present invention, these and other objects are obtained by providing an optical-type automatic analyzing and measuring apparatus which includes an optics/dispensing mechanism for dispensing reagents and samples, for irradiating the reaction system with light and for receiving the light scattered from the irradiated reaction system, an X-Y drive mechanism for transporting the optics/dispensing mechanism in two dimensions, a dispensing needle cleaning apparatus for cleaning the dispensing needle by subjecting it to jets of a cleansing agent and air, a lifting mechanism for lifting and replacing items such as covers protecting the reaction system, and a holder for reagents and samples.

The optics/dispensing mechanism, supported by guide rails and guide rollers constituting the X-Y drive mechanism, is transported in two directions by the drive mechanism to subject the surface of a reaction carrier undergoing electrophoresis to dispensing operations and to optical measurements of scatter intensity and the like. The optical system includes a lamp housing accommodating a light source for irradiating the surface of the reaction carrier, a light condenser, optical fibers for guiding the light, a lens housing for irradiating the prescribed area of the reaction carrier with light of uniform intensity, and a light receiving element for receiving light as is scattered from the irradiated surface. The dispensing needle is connected to a plurality of liquid supply sources by a pipe and is capable of being lowered to and raised from the surface of the reaction carrier in performing a dispensing operation.

The X-Y drive mechanism has X and Y sources of drive for driving the optics/dispensing mechanism in the X and Y directions along guide rails by means of driving belts. The dispensing needle cleaning apparatus is adapted to clean, by means of jetted liquid and air, the surface of the dispensing needle which repeatedly takes up reagents and samples and dispenses them at prescribed locations. The needle is cleaned by being raised and lowered through a conical cavity provided with a plurality of apertures for ejecting a cleansing solution and pressurized air toward the needle.

The lifting mechanism is adapted to open and close vessels by raising and lowering the vessel covers when the reaction carrier is to be supplied with reagents and samples by the dispensing needle, and when the surface of the carrier is to be subjected to optical measurement. Means for reading position optically are provided to assure that a lifter constituting the lifting mechanism will engage with hooks provided on the top surface of each cover.

The apparatus of the invention carries a reagent and sample holder whose base is provided with openings or recesses, having holes for liquid drainage, for receiving vessels such as bottles or test tubes filled with the reagents and samples.

The apparatus is further provided with buffer tanks and portions for accommodating them, and with electrodes to enable the apparatus to subject the reaction carrier to electrophoresis, thereby permitting even trace amounts of reaction products to be detected with great accuracy.

Other features and advantages of the invention will be apparent from the following description taken in conjunction with the accompanying drawings in which like reference characters designate the same or similar parts through the figures thereof.

BRIEF DESCRIPTION OF THE DRAWINGS

The accompanying drawings illustrate an embodiment of an optical-type automatic analyzing and measuring apparatus according to the present invention, in which:

FIGS. 18 through 23 illustrate a reagent and sample holder, in which

FIG. 18 is a plan view,

FIG. 19 a side section,

FIG. 20 a side section of a cover,

FIG. 21 a fragmentary enlarged view showing the right edge of the cover, depicted in FIG. 20, when the cover is attached, FIG. 22 a plan view of the portion shown in FIG. 21, and FIG. 23 a plan view useful in describing how the reagent and sample holder is covered by means of aluminum foil;

FIGS. 24 through 32 illustrate a buffer tank and a portion for receiving the buffer tank, in which FIG. 24 is a side view of the buffer tank, FIG. 25 an end view of the left end face of the buffer tank, FIG. 26 an end view of the right end face of the buffer tank, FIG. 27 a side view of an electrophoretic electrode mounted within the buffer tank, FIG. 28 a fragmentary side section, partially broken away, showing the buffer tank secured in the tank receiving portion, FIG. 29 a plan view of the same, FIG. 30 an end view, partially broken away, showing the left end face of the same, FIG. 31 an end view useful in describing how the buffer tank is turned, and FIG. 32 a side section showing the buffer tank when a tray is mounted thereon;

FIG. 36 is a fragmentary plan view illustrating how the tray is disposed on the apparatus; and FIG. 37 is a block diagram of electronic and hydraulic circuitry for controlling the operation of the apparatus of the present invention.

DETAILED DESCRIPTION OF THE PREFERRED EMBODIMENT

The present invention is particularly well-suited for the precise analysis and measurement, in continuous and automatic fashion, of antigen-antibody reactions using a variety samples.

The optical-type automatic analyzing and measuring apparatus of the present invention comprises an X-Y axis drive mechanism, an optics/dispensing mechanism, a dispensing needle cleaning mechanism, a lifting mechanism and a reagent/sample holder. Reference will now be had to the accompanying drawings for a structural and operational description of each of these constituent elements of the invention according to a preferred embodiment thereof.

[1] X-Y AXIS DRIVE MECHANISM

Figure 1:
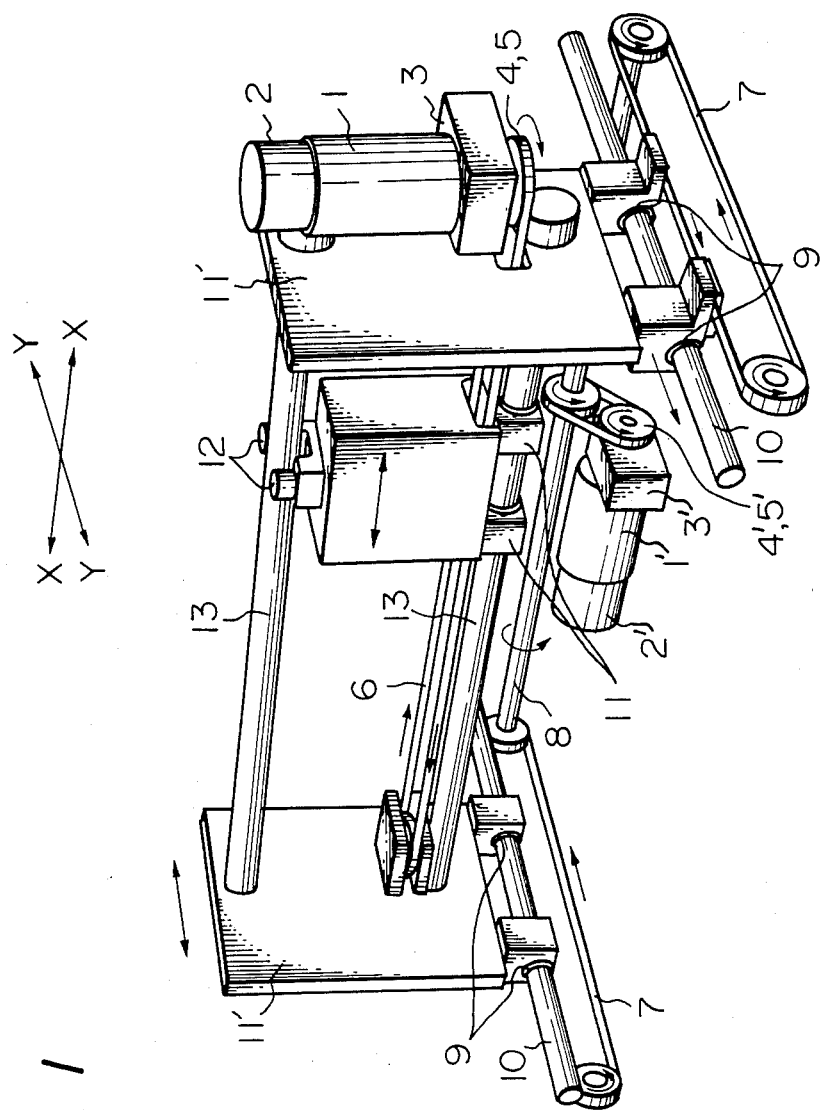
FIG. 1 is a perspective view schematically illustrating an X-Y axis drive mechanism for two-dimensionally transporting an optics/dispensing mechanism supported by the apparatus.

Referring FIG. 1, the X-Y axis drive mechanism includes drive motors 1, 1' constituting the sources of drive for the X and Y axes, respectively, encoder/decoders 2, 2' rotatively driven by the drive motors 1, 1', respectively, gear boxes 3, 3' driven by the drive motors 1, 1', sprockets 4, 4' driven by the motors 1, 1' via the respective gear boxes 3, 3', slip clutches 5, 5', a belt 6 associated with the sprocket 4 and slip clutch 5 for X-axis drive, a pair of belts 7 for Y-axis drive, a Y-direction drive shaft 8 for driving the belts 7, Y-axis guide shoes 9, a pair of Y-axis guide rails 10, X-axis guide shoes 11, X-axis guide rollers 12, and a pair of X-axis guide rails 13. The drive motors 1, 1' have respective rotary shafts which, in driving the gear boxes 3, 3', simultaneously rotate the corresponding encoder/decoders 2, 2' to control both travelling distance and travelling speed along the X and Y axes. The gear boxes 3, 3' rotate the sprockets 4, 4' upon reducing the rotational speed of the drive motors 1, 1' by a prescribed gear ratio. In the event of a malfunction or the application of an excessive force, the slip clutches 5, 5' are adapted to interrupt the transmission of rotational motion from the drive motors 1, 1' to the sprockets 4, 4' and to stop the motors, as will be described below.

The Y-axis drive shaft 8, rotated by the sprocket 4', drives the two belts 7, whereas the belt 6 is driven directly by the sprocket 4. The belts 7 are affixed to a portion of a Y-movement stage 11' so that the belts 7 and Y-movement stage 11' move in unison. The belt 6 is affixed to a portion of the optics/dispensing mechanism, described later, so that these may similarly move in unison. The Y-movement stage 11' is transported in the Y-direction on the two guide rails 10, via the guide bushes 9, by means of the Y-axis drive source acting through the belts 7. The optics/dispensing mechanism, on the other hand, supported on the guide rails 13 via the guide bushes 11 and guide rollers 12, is moved in the X-direction by the X-axis drive source acting through the belt 6. Such an arrangement makes it possible to move, position and stop the optics/dispensing mechanism at any desired location located in the X-Y plane.

Figure 2:
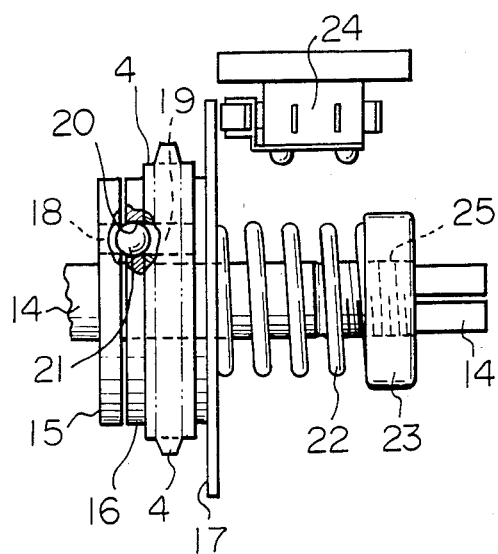
FIG. 2 is a fragmentary enlarged side view, partially broken away, showing a slip clutch provided on one end of a drive shaft mechanically connected to a drive motor.

As shown in FIG. 2, a clutch plate 15, a ball retaining plate 16, the sprocket 4 and a guide plate 17 are disposed on a drive shaft 14 extending from the gear box for driving/the sprocket 4. The clutch plate 15 is fixedly secured to the drive shaft 14, while the ball retaining plate 16, sprocket 4 and guide plate 17 are freely rotatable with respect to the drive shaft 14. Clutch plate 15 is provided with at least three holes 18 bored through the outer circumferential portion thereof, in alignment with at least three holes 19 similarly bored through the outer circumferential portion of the sprocket 4. The ball retaining plate 16 is provided with holes 20, each retaining a ball 21, at positions corresponding to the matched holes 18, 19. A spring 22 is compressed between the guide plate 17 and a stopper 23 which is threadedly attached to the drive shaft 14, whereby the guide plate 17, sprocket 4 and balls 21 are pressed toward the clutch plate 15 to operate in association therewith. In the event of a malfunction, or if the sprocket 4 should happen to be subjected to an excessive force, the balls 21 retained by the plate 16 will slip out of the holes 18 or 19 and the guide plate 17 will be forced to the right in FIG. 2, causing the guide plate 17 to actuate a switch 24 that will in turn halt the drive motor 1. The force applied by the spring 22 may be adjusted by moving the stopper 23 to the left or right along a threaded portion 25 formed on the drive shaft 14 to which the stopper 23 is attached.

Since correct correlation between the read-out of the encoder/decoder 2 and the positions along the X and Y axes ordinarily will be lost when the switch 24 is actuated to stop the motor, it is essential that the initial conditions be restored once the balls 21 have been properly re-engaged with the holes 18, 19. To accomplish this, the Y-movement stage and the optics/dispensing mechanism are moved back to the origin of the X and Y axes, after which the encoder reading is reset.

It should be noted that the slip clutch arrangement of the slip clutch 5' is identical with that of the slip clutch 5 just described. A description of said arrangement is therefore omitted to avoid prolixity.

[2] OPTICS/DISPENSING MECHANISM

Figure 3:
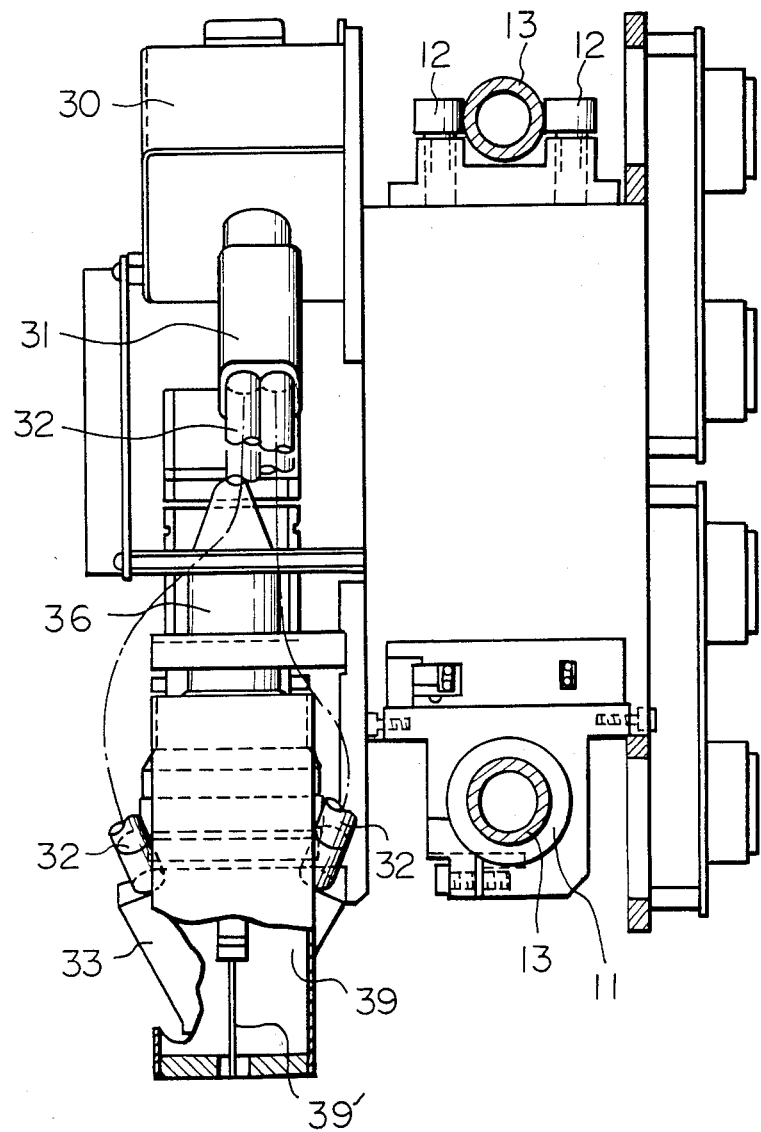
FIG. 3 is a side view, partially broken away, showing the optics/dispensing mechanism.
Figure 4:
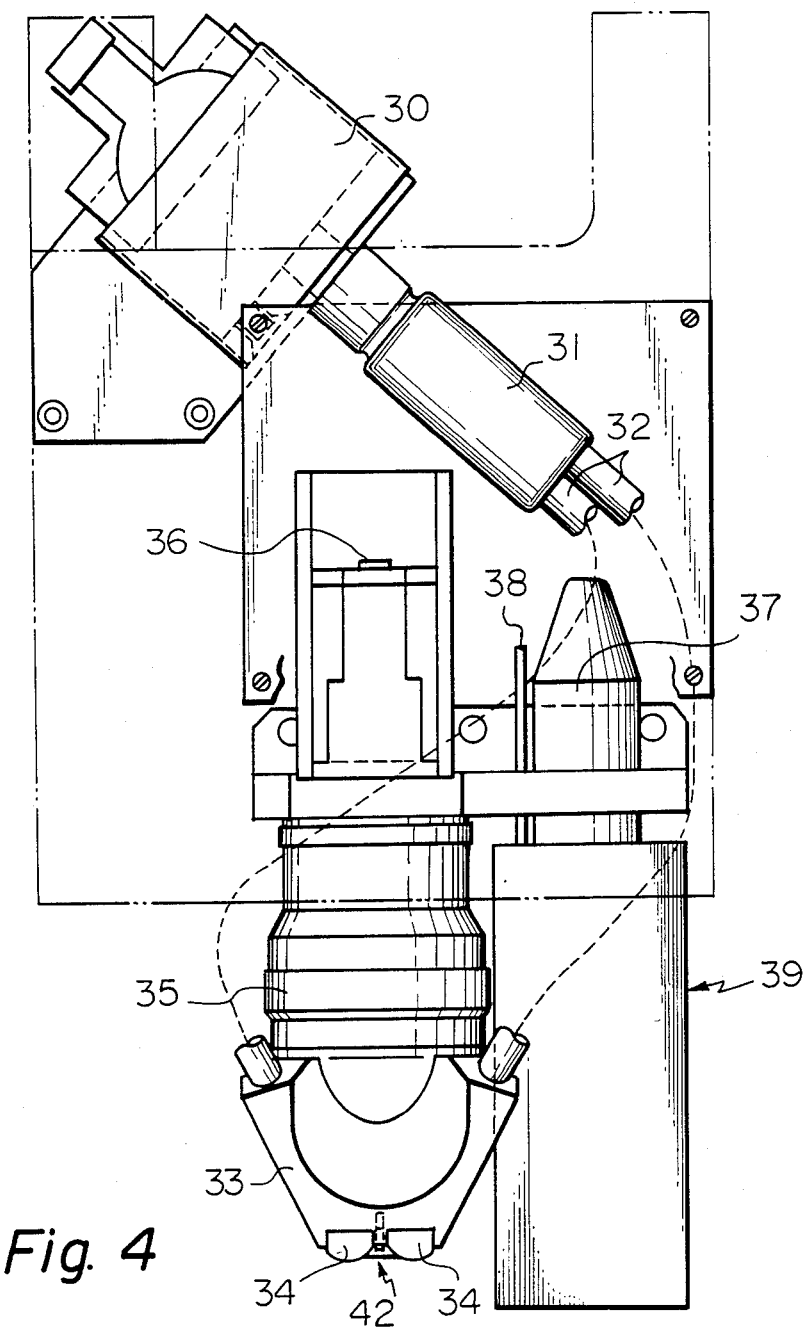
FIG. 4 is a front view of the mechanism shown in FIG. 3.

The optics/dispensing mechanism block, illustrated in FIGS. 3 and 4, also carries a lifting mechanism not shown. As will be described later, the lifting mechanism is adapted to lift an item such as a cover in the same fashion as the human hand. The block carrying these mechanisms can be moved to any position in the X-Y plane by the X-Y drive mechanism, as described above, in order to perform a dispensing operation as well as optical measurements.

As shown in FIGS. 1 and 3, the optics/dispensing mechanism is supported on the pair of guide rails 13 by means of the X-axis guide bushes 11 and X-axis guide rollers 12. The optics/dispensing mechanism, as shown in FIGS. 3 and 4, includes an optical system composed of such elements as a lamp housing 30, a condenser and light distributor 31, light guiding glass fibers 32, an irradiation lens housing 33, irradiation lenses 34, an objective lens 35, and a light receiving element 36. The optics/dispensing mechanism further includes a dispensing device 39, disposed just to the right of the optical system in FIG. 4, incorporating a dispensing needle 39', shown in the broken away portion of FIG. 3, which can be raised and lowered when necessary. Also included are a pulse motor 37 for driving the dispensing needle 39' up and down, and a pipe 38 for fluid transfer.

Figure 5:
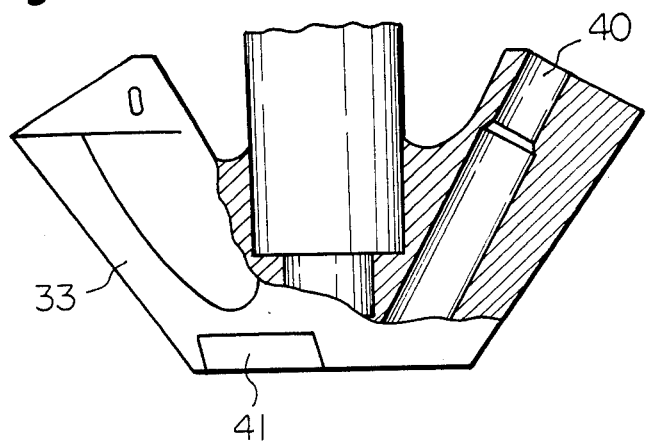
FIG. 5 is a fragmentary enlarged side view, partially broken away, showing an irradiation lens housing.
Figure 6:
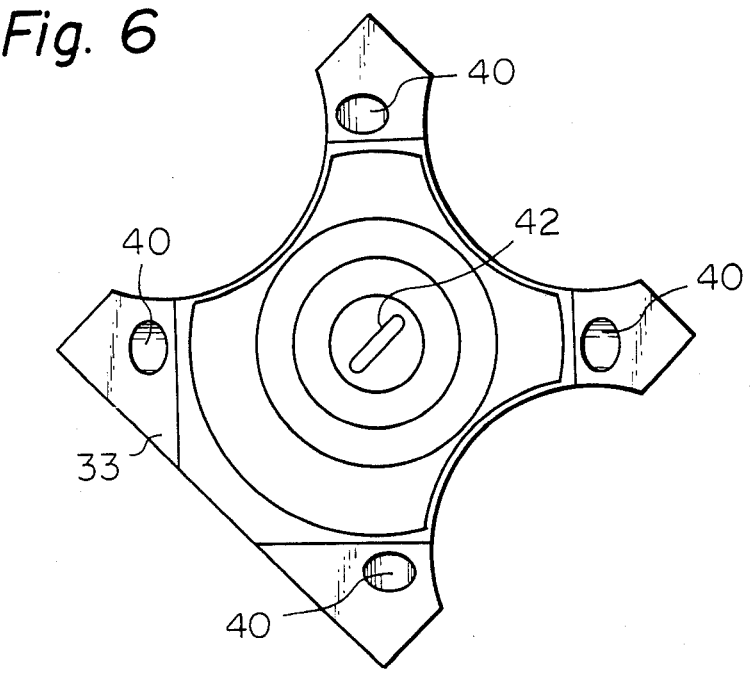
FIG. 6 is a plan view of the irradiation lens housing.

FIGS. 5 and 6 illustrate the irradiation lens housing 33, adapted to perform optical detection and measurement with excellent efficiency and great accuracy. Light emitted from the lamp housing 30 in FIG. 4 is evenly distributed among four of the glass fibers 32 by the distributor 31, whence the light is transmitted to four apertures 40 formed in the irradiation lens housing 33.

In the present embodiment, a linear image sensor having a row of a multiplicity of photoelectric converting elements is employed as the light receiving element in order to exploit the scanning operation of the X-Y drive mechanism effectively. Accordingly, the irradiation surface for optical measurement will require a fine, uniform beam of light. The method of irradiation by causing convergence of a fine filament image gives rise to a variance in luminance, however, and is undesirable as a result thereof.

Figure 7:
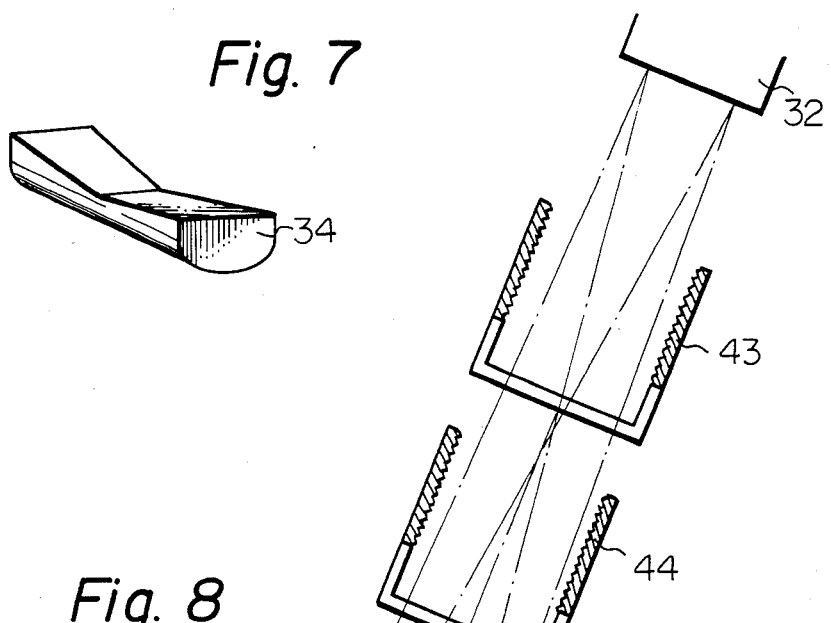
FIG. 7 is a perspective view of the irradiation lens housing.

Ordinarily, light transmission is preferred when reading, say, the pattern of the substance under examination. In the present embodiment of the apparatus, however, the provision of the light source at the base of the apparatus would complicate its structure, and the effect of the heat given off by the light source would be a factor that could not be neglected. Accordingly, the apparatus as embodied herein requires the adoption of a system based on the light-scattering technique. Meanwhile, in order to improve the read-out sensitivity and SN ratio, a greater light intensity is required. This in turn requires light from a multiplicity of directions, and not just obliquely incident light from one direction. Such an expedient will prevent a non-uniformity in the quantity of light caused by differences in the optical path length. Specifically, as depicted in FIG. 5, recesses 41, of which only one is shown, are formed in the irradiation lens housing 33. Fixedly secured within these recesses are the irradiation lenses 34, as illustrated in FIG. 4. Each irradiation lens 34, as shown in FIG. 7, has a semi-circular cross section and inclined flat surfaces that converge toward the center of the lens to form wedge-shaped bodies that meet at their narrower ends. With such an arrangement, light for the purpose of examination scattered from the irradiation surface will pass through a slit 42 provided between the two lenses 34, 34, as shown in FIG. 4.

Figure 8:
FIG. 8 is an illustrative view useful in describing the optical path within the irradiation lens housing.

Referring now to FIG. 8, the irradiating light beam from the glass fiber 32 is removed of extraneous light by means of slits 43, 44 and passes through the irradiation lens 34 in the form of a light beam having a substantially rectangular, elongate cross section. The light, in passing through the lens 34, is converged and corrected in terms of optical path length and irradiates a target 45, disposed on the irradiation surface, in substantially uniform fashion. Strictly speaking, however, a slight disparity in the quantity of light in the front and rear and at the right and left sides of the irradiation surface in FIG. 8 does have a considerable influence upon measurement. Accordingly, in order to achieve even greater accuracy in measurement, light irradiates the target from the left as well in FIG. 8, although this is not shown, and the second lens 34 is provided, thereby irradiating the target from a total of four directions. As a result, the detection sensitivity and SN ratio can be improved by uniformalizing the intensity of the light incident upon the irradiation surface.

Figure 9:
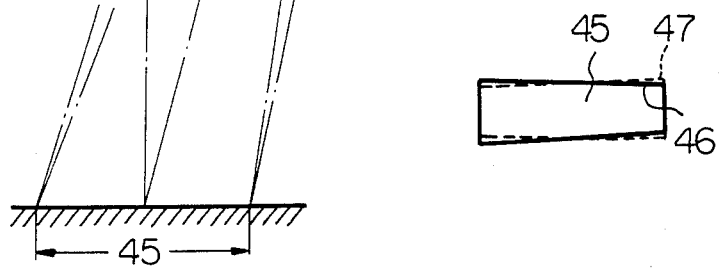
FIG. 9 is an illustrative view useful in describing the irradiation surface of a uniform luminous flux compensated from the left and right.

FIG. 9 shows an example of the light pattern 46 for irradiation of the target 45 from the right, and of the light pattern 47 for irradiation of the target from the left. In either the case the light forms a trapezoidal pattern on the surface target 45, but the two patterns compensate each other to make up for the lack of symmetry on the left and right, and light incident upon the irradiation surface at predetermined angles can be obtained.

Although effects similar to the above can be obtained through use of a ring-shaped lens, the foregoing arrangement is preferred since the target is rectangular in shape. In other words, the ring lens would irradiate portions not requiring irradiation, thereby influencing the specimen. Moreover, such a lens is difficult to machine and is therefore more costly to manufacture than the lens shown in FIG. 7.

Figure 10:
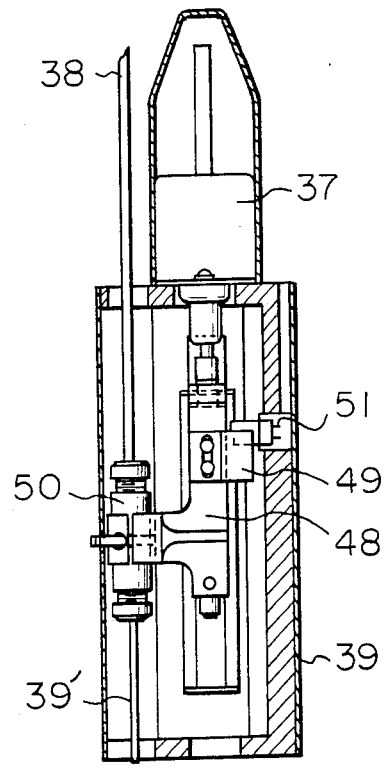
FIG. 10 is an enlarged side view illustrating a dispensing mechanism.

The dispensing device 39, shown carried on the optics/dispensing mechanism in FIG. 3, is illustrated in greater detail in FIG. 10. The dispensing device 39 includes a raising and lowering mechanism 48 which the pulse motor 37 moves up and down in accordance with a received signal. The raising and lowering mechanism is provided with an optical shutter 49 for actuating a limit switch 51, and with a hydraulic joint 50 for fixing the pipe 38 and dispensing needle 39' against vertical motion. The dispensing needle 39' is lowered by an amount commensurate with the number of pulses applied to the pulse motor 37 from the reset position of the limit switch 51 and shutter 49, the vertical movement of the needle being specified by the number of pulses at all times. The positional relationship between the dispensing needle 39' and the optical system is always constant, and the needle is capable of being moved to any position identified by the optical system, and of being lowered at said position.

[3] DISPENSING NEEDLE CLEANING MECHANISM

Figure 11:
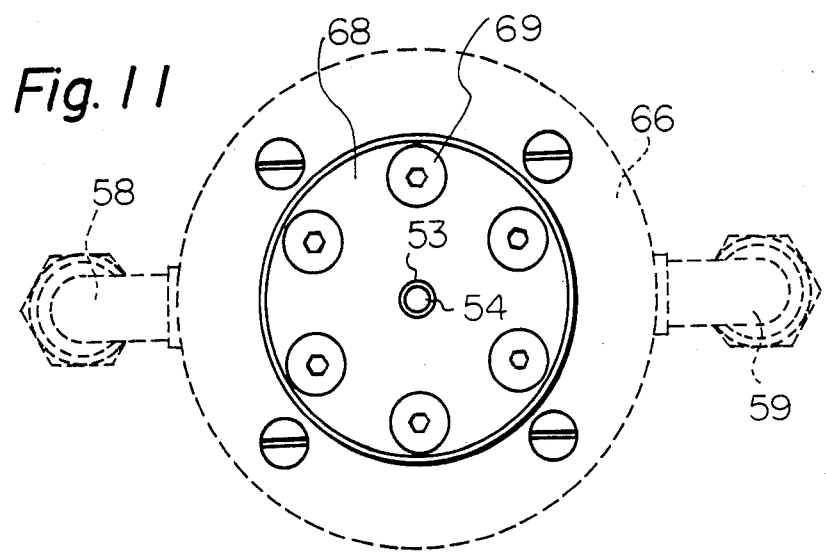
FIG. 11 is a top view illustrating a dispensing needle cleaning mechanism.
Figure 12:
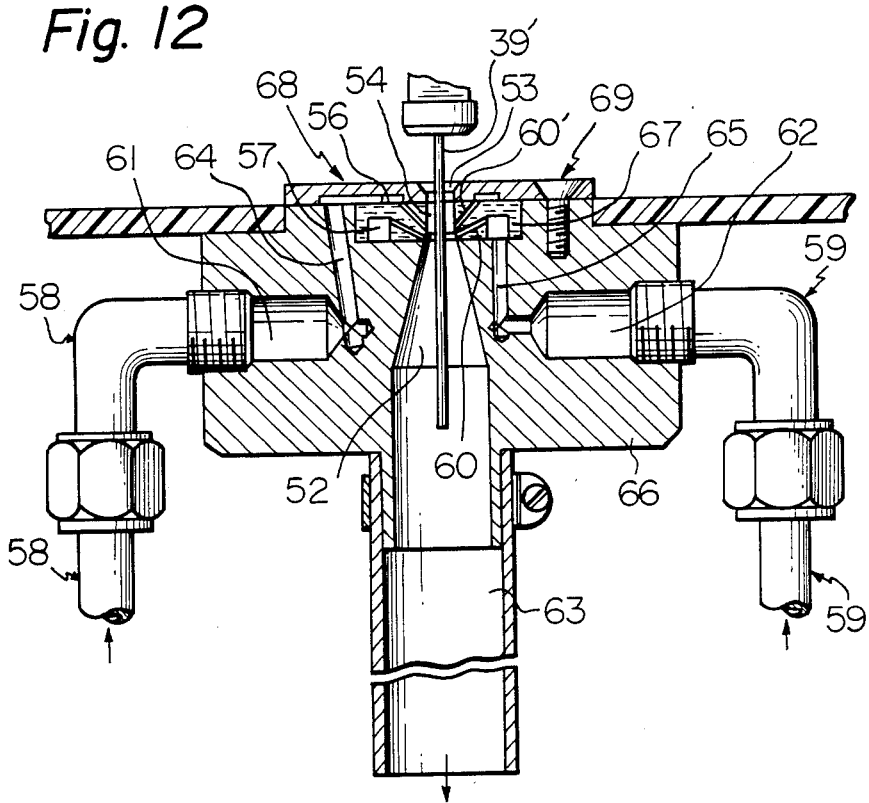
FIG. 12 is a side section of the mechanism shown in FIG. 11.

FIGS. 11 and 12 illustrate the dispensing needle cleaning mechanism, so arranged that the top surface thereof lies situated substantially flush with the irradiation surface mentioned above. Since the dispensing needle 39' is designed for measuring out quantities of a sample and for transport, wherein it may take up predetermined quantities of a sample and deliver the sample to a prescribed location, as well as dispense a reagent at prescribed locations, problems that are likely to occur are contamination between samples, the introduction of air bubbles and the admixing of reagents, all of which can have detrimental effects. In particular, contaminants attaching to the exterior of the dispensing needle may induce rusting and degrade the accuracy of quantitative determinations.

In view of the foregoing, it is preferred that cleaning be accomplished by use of a physioligical salt solution or distilled water, followed by wiping with a piece of clean, fresh paper. Since such is not readily feasible with an automatic analyzer, however, the following set-up and method may be employed.

In the embodiment of the invention illustrated in FIG. 12, the cleaning mechanism comprises a main body 66 having an air inlet 61, a liquid inlet 62, a centrally located conical cavity 52, an outlet 63, a passage 64 connected to the air inlet 61 and a passage 65 connected to the liquid inlet 62, an intermediate section 67 set into the upper surface of the main body 66 at the central portion thereof and having a plurality of lower passages 60 and a plurality of upper passages 60' for ejecting a rinsing liquid and air, respectively, and a cover 68 for covering the main body 66 and intermediate section 67. The cover 68 is sealed tightly in place by screws 69 to prevent the leakage of gases and liquids. The cover 68 has a centrally located opening 53 which communicates with a central passage 54, provided in the intermediate section 67, of a diameter permitting the passage of the dispensing needle 39' therethrough. The lower rinsing liquid ejection passages 60 and the upper air ejection passages 60' slant downwardly and open into the passage 54 near where it meets the conical cavity 52. The lower passages 60 communicate with an annular passage 57 provided in the intermediate section 67 and which in turn communicates with the rinsing liquid inlet 62, and the upper passages 60' communicate with an annular passage 56 provided in the cover 68. The passages 60' communicate with the air inlet 61. Pressurized air is introduced into the upper passages 60' from a pipe 58 leading to the air inlet 61, and the rinsing liquid is fed into the lower passages 60 from a pipe 59 connected to the rinsing liquid inlet 62.

In operation, the rinsing mechanism is transported by the X-Y drive mechanism to position the dispensing needle 39' over the center of the opening 53, and a signal is applied to the pulse motor 37 of the dispensing mechanism 39 to lower the dispensing needle 39' down to a predetermined position within the cavity 52. When said position has been reached, the applied signal causes the dispensing needle 39' to be raised while the needle is sprayed with the rinsing liquid ejected by the lower passages 60. After this operation has been repeated once or several times, the dispensing needle 39' is lowered again and then slowly raised while being subjected to streams of air ejected by the upper passages 60', whereby the rinsing liquid is completely blown off the needle. This affords the same effect as wiping the needle with paper or cloth. Rinsing of the interior of the dispensing needle 39' is performed by the alternating passage of rinsing liquid and air therethrough when the needle is at its lowermost position. The last step is the penetration of air to remove the liquid.

The foregoing operation is repeated from one to several times depending upon the particular requirement. For example, when taking up a sample or a reagent and applying it in a predetermined amount to a number of locations, the exterior of the dispensing needle need be rinsed only once and then blown clean only once to completely remove droplets from the outside of the needle. The result is a marked increase in the accuracy of quantitative determinations, without any danger of the sample or reagent dripping from the needle.

Preferably, from four to six of the upper and lower passages 60', 60 are provided to assure uniform cleaning of the dispensing needle exterior. Furthermore, the angle of inclination of the upper passages 60' is set in such a manner that the point at which they would intersect by extending them is positioned within the conical cavity 52 and slightly higher than the point at which the lower passages 60 would intersect, thereby assuring that the needle will be blown clean without misses. In addition, the provision of the conically shaped cavity 52 directs the ejected air and liquid downwardly toward the outlet 63 to prevent the same from being blown out of the opening 53. The outlet 63 may therefore operate under a condition where it is open to the atmosphere, without requiring the application of suction pressure to the outlet.

[4] LIFTING MECHANISM

Figure 13:
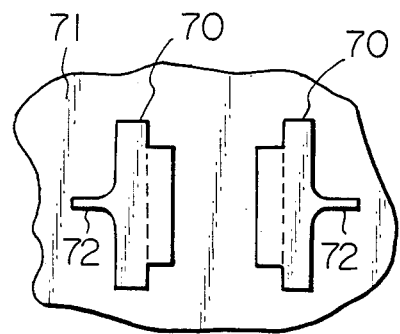
FIG. 13 is a fragmentary enlarged view of a cover.
Figure 14:
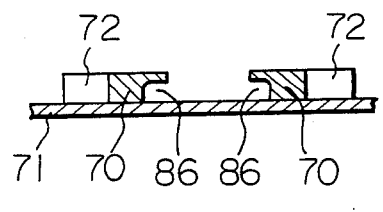
FIG. 14 is a side section of the cover shown in FIG. 13.

The lifting mechanism is adapted to lift a cover provided for the purpose of preventing the evaporation of water contained in the reaction carrier which is accommodated in a vessel, and to replace the cover following the dispensing of the prescribed reagent or sample or upon the completion of an optical measurement. The lifting mechanism can even lift and transport an object other than the cover and both raise and lower the object at a predetermined location. The object, in order to be raised, is provided at substantially the center of gravity thereof with a pair of hooks 70 having a substantially reverse L-shaped cross section, as shown in FIG. 14. In FIGS. 13 and 14, the hooks 70 are shown affixed to the top surface of a flat cover 71 by means of an adhesive or the like. The outwardly facing side of each hook 70 is provided with a light shielding plate 72 to interrupt a light beam for the purpose of confirming whether the cover has actually been lifted. It is permissible to form both the hook 70 and the shielding plate 72 of an opaque synthetic resin.

The lifting mechanism should be secured to the optics/dispensing mechanism at a position where the lifted object, such as the cover 71, will not impede the dispensing operation or the optical measurement, and so that the positional relationship among the lifting mechanism, optical system and dispensing mechanism will be fixed at all times.

Figure 15:
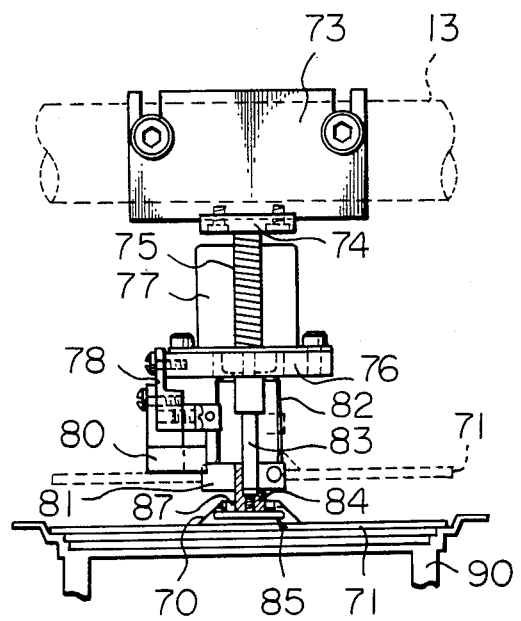
FIG. 15 is a front view illustrating a lifting mechanism.
Figure 16:
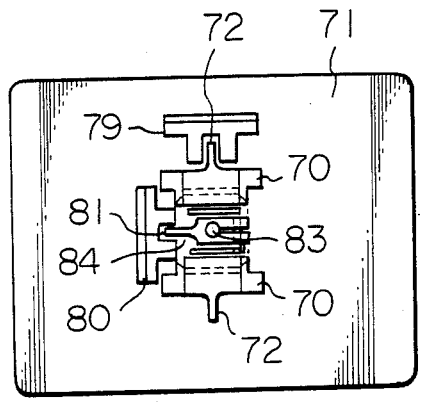
FIG. 16 is a plan view showing the end portion of the lifting mechanism.
Figure 17:
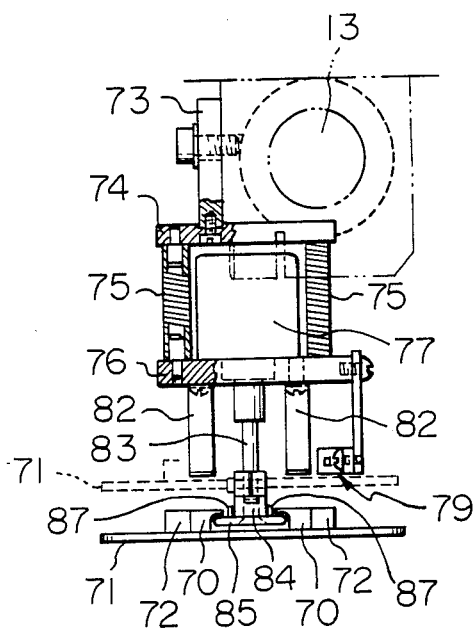
FIG. 17 is a side view of the lifting mechanism.
Figure 18:
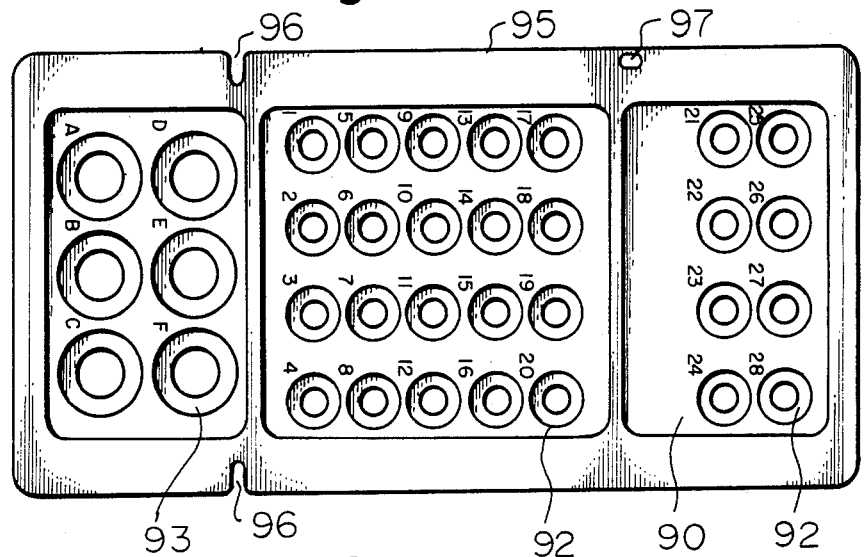
Figure 19:
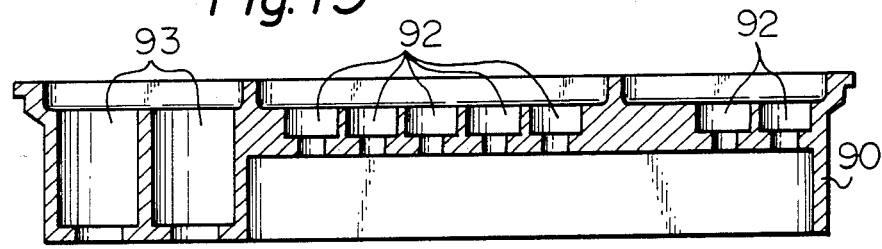
Figure 20:
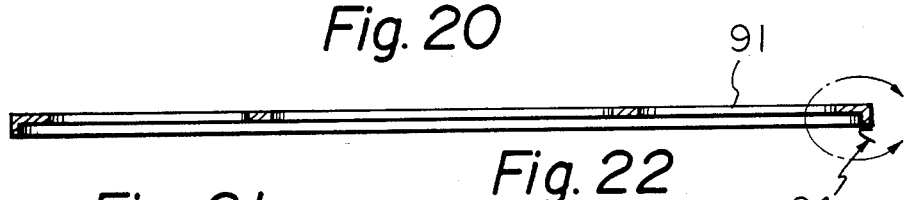
Figure 21:
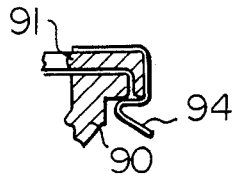
Figure 22:
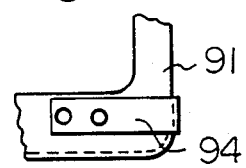

Reference will now be had to FIGS. 15 through 17 to describe the construction and operation of the lifting mechanism. Support plates 73, 74 are fixedly secured to a portion of the optics/dispensing mechanism supported on the rails 13, and an attachment plate 76 is suspended from the support plates 73, 74 by means of buffer springs 75. Provided on the attachment plate 76 are the pulse motor 77, optical sensing switches 78, 79, a guide 80 for guiding a light shielding plate 81 to the sensing switch 78, and leaf springs 82 for retaining the cover 71 in a horizontal attitude. An arm 83 is coupled at one end to the pulse motor 77 for vertical movement thereby. Affixed to the other end of the arm 83 is that end of a flat lifter 84 having a light shielding plate 81. The other end of the lifter 84 has a flat plate 85 in the form of a rectangle with rounded corners. The flat plate 85 has thickness and width dimensions that allow it to readily penerate a space 86, shown in FIG. 14, defined by the opposing hooks 70 provided on the cover 71. Guide plates 87 for controlling attitude are provided on the upper portion of the flat plate 85 to prevent the lifted cover 71 from rotating and from tilting from side to side.

The sensing switch 78 senses the position of the light shielding plate 81 on the lifter 84 affixed to the end of the arm 83 and stops the upward movement of the lifter at the upper end of its stroke. The sensing switches 79 sense the light shielding plates 72 provided on the cover 71 and are used to judge whether the cover has been lifted.

In the operation of the lifting mechanism, the mechanism is transported by the X-Y drive mechanism until its center arrives at a position just short of the hooks 70. The pulse motor 77 is then actuated to lower the arm 83 a distance commensurate with the number of pulses applied to the motor, after which the X-Y drive mechanism is so controlled as to bring the lifter 84, located at the end of the arm 83, into the space between the opposing hooks 70 provided on the cover 71. When the pulse motor 77 is instructed to raise the arm 83, the cover 71 is lifted, abuts against the leaf springs 82 and is held at the position where the light shielding plate 81 is detected by the sensing switch 78, namely at the position indicated by the dashed lines. The sensing switches 79 now sense whether the cover is in the fully raised position. If it is, the dispensing operation and optical measurements may be carried out. Upon the completion thereof, the arm 83 is lowered again to restore the cover 71 to its original position.

The buffer springs 75 mentioned above are tension springs that do not have any clearance between the adjacent coils in the wire constituting them. The springs will hold the attachement plate 76 at a predetermined level as long as the mechanism is not subjected to an excessive force. For instance, the springs 75 will tilt or stretch in the event of a shock or impact to prevent damage to the lifting mechanism or surrounding objects, and will return to their original attitudes when conditions have returned to normal.

In accordance with the foregoing construction, therefore, an object can be raised merely by providing it with the pair of hooks 70, lowering the lifting mechanism to engage with the hooks, and then raising the mechanism to lift the object. This enables an object such as a cover to be lifted and replaced reliably in a very simple manner.

[5] REAGENT AND SAMPLE HOLDER

As shown in FIGS. 18 through 23, the reagent and sample holder comprises a holder main body 90 and a cover 91. When in use, the reagent and sample holder holds an array of open reagent bottles, test tubes, viles and the like, which are covered by a shield of aluminum foil A1, shown in FIG. 23, interposed between them and the cover 91 in order to keep out dust and other contaminants and to prevent evaporation of the reagents and samples. The dispensing needle 39' is lowered to puncture the aluminum foil and take up the desired reagent or sample.

The holder body 90 is a molded body made of synthetic resin or the like and has holes 92, 93 formed in its floor for retaining bottles or test tubes, for facilitating washing and for allowing spilt liquids to drain away. Ordinarily, the holes 93 hold an array of reagent bottles, while the holes 92 are for retaining small, disposable-type test tubes made of synthetic resin. Affixed to two opposing edges of the cover 91 are a plurality of leaf springs 94 for preventing the peeling of the aluminum foil, whose outer edges are sandwiched between the holder body 90 and cover 91. The cover 91 comprises a stainless steel plate having windows of considerable area to give access to the bottles and test tubes via the aluminum foil, as shown in FIG. 23, and is sized so that the surface of the cover will not obstruct the two-dimensional travel of the dispensing needle 39'. Notches 96 and an oblong hole 97 for engaging with positioning pins, not shown, are provided at the edge 95 of the holder body 90 asymmetrically, or only on one side thereof, to assure that the holder will be positioned and oriented correctly when set in place. When removing the cover 91, the leaf springs 94 are lifted obliquely outwards.

It is preferred that the reagent and sample holder be provided adjacent the dispensing needle cleaning mechanism, as illustrated in FIG. 23. The reason is to reduce the distance between these two units since the dispensing needle 39' is always carried to the cleaning mechanism to have its exterior cleaned of excess liquid immediately after the needle takes up a reagent or sample.

The apparatus of the invention having the foregoing construction, comprising the (1) X-Y drive mechanism, (2) optics/dispensing mechanism, (3) dispensing needle cleaning mechanism, (4) lifting mechanism and (5) reagent and sample holder, makes it possible to measure, continuously and automatically without human intervention, the temporal change in the formation process of a bacterial colony. In such case it suffices merely to fill Petri dishes with a culturing gel and to provide the Petri dish covers with the hooks 70 described above. This will enable the apparatus of the invention to automatically lift the covers from a plurality of the Petri dishes one at a time, inoculate the Petri dishes with bacteria, replace the covers, optically scan the cultures intermittently, and measure the growth of the colonies through photography or numerically by means of pattern recognition. The apparatus of the invention also makes it possible to measure, in similar fashion, bactericidal ability with respect to different types of bacteria. The apparatus also is effective in the area of clinical medicine where samples are subjected to immunological measurements for determination of blood type, immune globulin measurement and serum protein measurement by means of the SRID method (radial immunodiffusion), and in the measurement of various antigen-antibody reactions, such as in experiments on the agglutination reaction in blood.

The apparatus of the invention obviously is effective in measuring fast-occurring reactions, but also may find application in the periodic measurement of reaction processes that may take as long as from several hours to several dozen hours. In either case, merely loading the proper program in a sequence determining unit of the apparatus will enable the addition of reagents and the necessary measurements to be made automatically in the desired fashion.

In one aspect of the invention, which will be described hereinbelow, buffer tanks and a tray may be included in the apparatus to provide an automated and highly accurate electrophoretic measuring device. By combining such feature of the invention with the immunological measurements mentioned above, the apparatus of the invention may also find use as an automated electrophoretic apparatus for immunological research.

[6] BUFFER TANKS

The requirement for electrophoresis is an electrophoretic support such as cellulose acetate film, agar-agar, agarose or the like, and a pair of buffer tanks each accommodating electrodes and a buffer solution. In the electrophoresis of a sample, the support bearing the sample is disposed astride the buffer tanks, and an electric current is passed through the support via the buffer solutions in each tank, causing fractionation of the various components contained in the sample due to differences in the mobility of these components, which depends upon their particular electric charge. The fractionated components are then dyed by a reagent such as a deep coloring solution, after which the density or fractionated pattern is read by optical means. To conduct immunological measurements, antigens or antibodies that react with the fractionated components are used to form precipitates, which in turn form a pattern of sedimentation lines that are optically read.

Reference will be had to FIGS. 24 through 32 to describe the buffer tanks and portions for accommodating them.

Each of the buffer tanks 100 has the shape of a slender rectangular prism, open at the top, so that a plurality of supporting bodies may be disposed simultaneously. The buffer tank has end portions 101, 102 formed to include notches 103 at their base portions. The end portions 101, 102 are further provided with arcuate grooves 104, 105, respectively, the groove 105 communicating with a hole 105'. These notches, grooves and hole serve to secure the buffer tank, in a manner to be described below, within an accommodating portion when the tank is pivoted about the notches 103.

Figure 27:
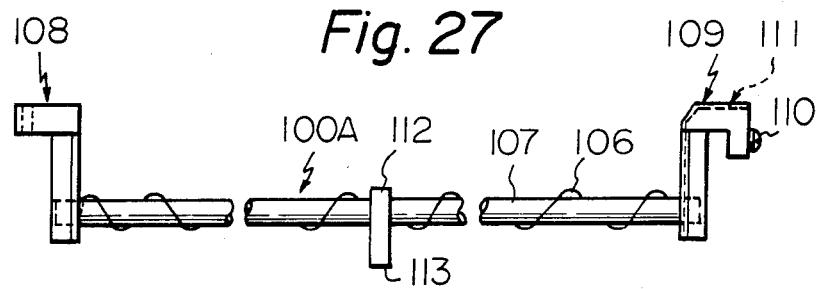

FIG. 27 illustrates an electrode unit 100A fixedly received within the buffer tank 100. A bare electric wire 106 made of platinum or the like is affixed to a supporting rod 107 affixed at both ends to the buffer tank 100 by fixing members 108, 109. The fixing member 109 is provided with an electrical contact 110 in such a manner that the contact 110 will be situated on the outer side of the buffer tank end face 102 when the supporting rod 107 is affixed to the buffer tank. The electrical contact 110 is connected to the wire 106 by a wire 111. A support piece 112 is provided at substantially the central portion of the supporting rod 107 to prevent the rod from bending, the base 113 of the support piece 112 abutting against the floor of the buffer tank 100.

Figure 28:
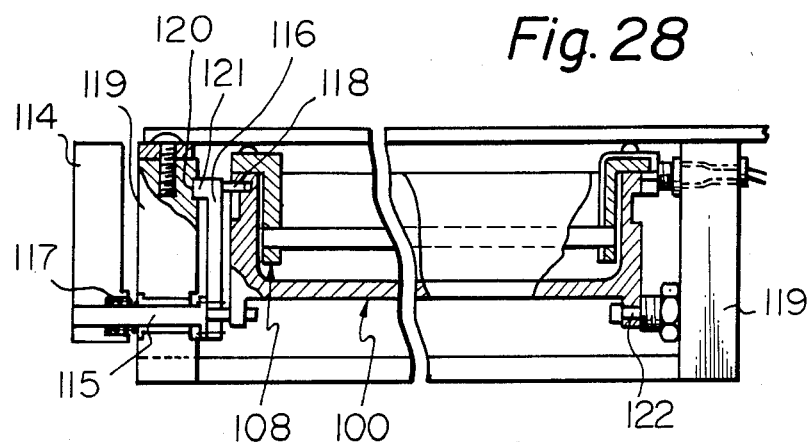
Figure 29:
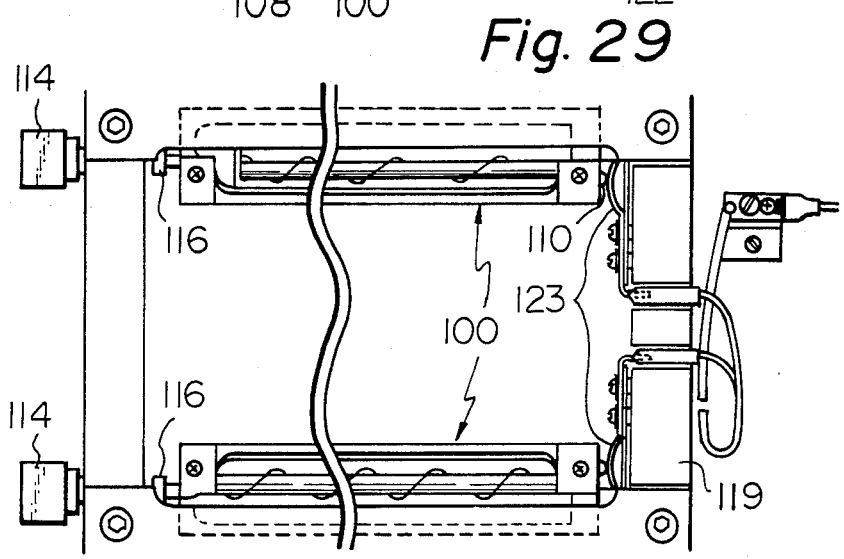
Figure 30:
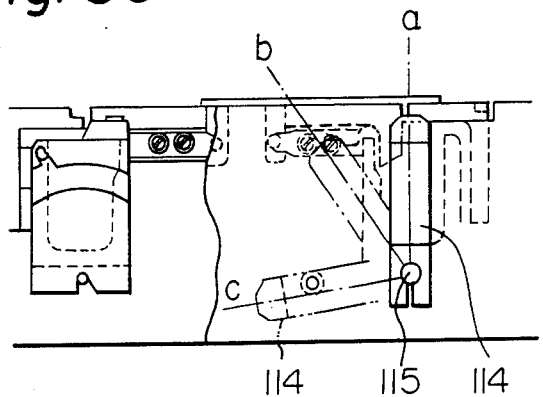
Figure 31:
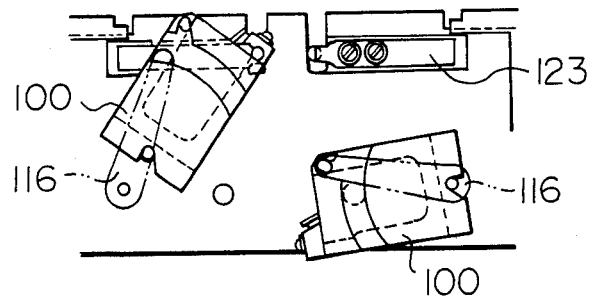

FIGS. 28 and 29 are useful in describing buffer tank accommodating portions provided in the main body of the apparatus for the purpose of securing each of the buffer tanks 100. Each buffer tank accommodating portion is provided with a knob 114 for securing and rotating the corresponding buffer tank 100, a shaft 115 affixed to the knob 114, and a rotating piece 116. A spring 117 is provided to thrust the shaft 115 outwardly at all times. The end of the rotating piece opposite the shaft 115 is equipped with a projection 118 on one side thereof for engaging with the hole 105' in the end face 101 of the buffer tank, shown in FIG. 25, and with a projection 121 on the other side thereof for engaging with a hole 120 provided in the main body of the apparatus, indicated at numeral 119. The buffer tank accommodating portion further includes a shaft 122, provided on the main body 119 at the side opposite the knob 114, for supporting the end face 102 of the buffer tank 100 by engaging with the notch 103 provided in said end face, as illustrated in FIG. 26. The shafts 115, 122 thus support the buffer tank 100 at the base portion thereof via the notches 103.

Attached to the main body 119 of the apparatus is a leaf spring-type contacting piece 123, shown in FIG. 29, which contacts the electrical contact 110 provided on the buffer tank 100 for supplying the electrode current. The contacting piece 123 is so positioned as to touch the contact 110 only when the buffer tank 100 is in the upright attitude. More specifically, when the knob 114 is at the position a in FIG. 30, the buffer tank 100 is upright, allowing current to flow into the electrode via the contacting piece 123 and contact 110. When the knob 114 is in position b, contact is broken. At the same time, the projection 121 on rotating piece 116 shown in FIG. 28 slips into the hole 120 provided in the main body 119, whereby the knob 114 is thrust to its leftmost position in FIG. 28 owing to the action of the spring 117. As a result, the projection 118 on the other side of the rotating piece 116 disengages from the hole 105' provided in the end face 101 of the buffer tank 100, allowing the buffer tank to be readily extracted. When the knob 114 is turned to position c in FIG. 30, the rotating piece 116 disengages the projection 121 from the hole 120, so that the knob is moved to the right in FIG. 28, causing the buffer tank 100 to tilt as the knob is turned. This allows the contents of the tank, namely the buffer solution, to be poured out toward the base of the apparatus, as shown on the right side of FIG. 31. The knob 114 thus fixes the buffer tank 100 when in position a, detaches the tank when in position b, and pours out the contents of the tank when in position c, all in a very simple manner. This facilitates the replacement of the buffer solution as well as the removal of the tank for washing.

It should be noted that only one of two buffer tanks 100 is illustrated in FIGS. 24 through 28. The other tank has the same construction, but is symmetrical with respect to the first.

[7] TRAY

Figure 32:
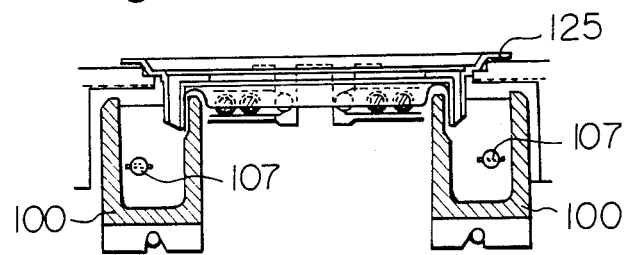

As shown in FIG. 32, one of a plurality of trays 125 is provided for accommodating an electrophoretic supporting body made of agar-agar or agarose. For electrophoresis using a cellulose acetate film, on the other hand, the film may be provided in the form of a simple sheet, without necessitating the tray of the illustrated embodiment. For other simple bacteriological measurements, moreover, the buffer tanks may be dispensed with, and Petri dishes of a different configuration may be employed.

Figure 33:
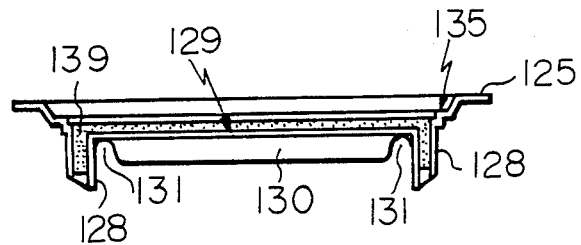
FIG. 33 is a side section of the tray.
Figure 34:
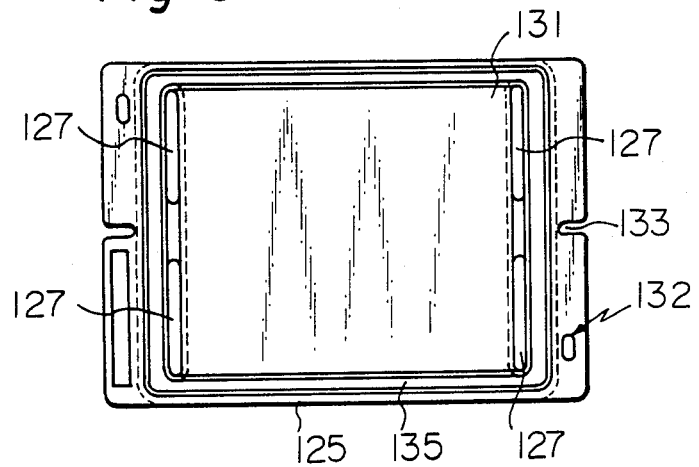
FIG. 34 is a plan view of the tray.

In accordance with the illustrated embodiment, however, use is made of synthetic resin trays for accommodating a gel of agar-agar or agarose, which are well-suited for application to immunoelectrophoresis, as well as covers for the trays. FIG. 33 is a sectional view illustrating one of the trays 125, FIG. 34 a plan view, and FIG. 35 a plan view of one of the covers, designated at 126.

The tray 125 has leg portions 128 at the right and left sides of the floor 129 thereof, each leg having an opening 127 communicating the top surface of the floor with the open lower end of the leg. The slightly recessed floor 129 of the tray 125 is flat and its bottom surface is provided with elongate ribs 130 for increased mechanical strength. The tray 125 also has a step portion, at a level higher than the recessed floor 129, for receiving the cover 126. Notches 131 are provided in the ribs 130 at both sides thereof but are so formed that the floor 129 of the tray will not contact the upper edge of the buffer tank. Agar-agar or agarose 139 is charged into the openings of the leg portions 128 down to their lower extremities, and covers the floor 129 of the tray to a flat, uniform thickness. The upper edge of the tray 125 is provided with oblong holes 132 and notches 133 for engaging positioning pins, not shown.

Figure 35:
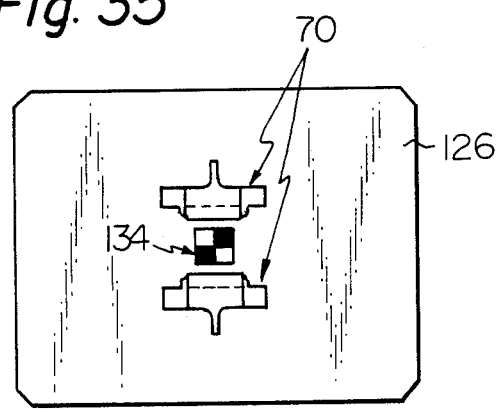
FIG. 35 is a plan view of a cover.

The cover 126, shown in FIG. 35, is provided with the pair of opposing hooks 70 described earlier in the discussion of the lifting mechanism, and with optical positioning marks 134, when necessary. The cover is placed on the above-mentioned step portion 135 located above the floor of the tray. As shown in FIG. 32, the tray 125 is disposed across the buffer tanks 100 with the openings 127 in the legs 128 of the tray immersed below the liquid level of the buffer solution, whereby an electrical connection is established between the buffer solutions through the gel.

The overall arrangement of the elements constituting the apparatus according to the present invention may be understood from FIG. 36, in which it is seen that the trays 125, along with the dispensing needle cleaning apparatus [3] and reagent and sample holder [5], described above, are disposed at prescribed positions on a tray horizontally retained by the main body 119 of the apparatus. The X-Y drive mechanism [1] carrying the optics/dispensing mechanism is secured to a portion of the main body 119 in such fashion as to bestride the mechanisms [3], [5], the trays 125, etc. Of the plurality of trays 125, that located at the lower left corner is shown to be provided with apertures 137 to permit the injection of samples for immunoelectrophoresis, and with grooves for antiserum.

One example of the electronic and hydraulic circuitry for operating the apparatus is illustrated in FIG. 37. The portion enclosed by the broken line is the scanning portion of the apparatus and is composed of a light source 150, a light receiving unit 151, a sensing circuit 152, a light source power supply 153, a dispensing mechanism 154 and a lifting mechanism 155. Scanning is performed by drive sources 156, 157 for the X and Y axes, respectively. A power supply 159 supplies a buffer tank 158 with a voltage for electrophoresis. An electronic control circuit 160 controls the operation of the units 153 through 157, and is adapted to drive a hydraulic control unit 161. The latter controls the delivery of pressurized air from a pump 162, as well as the delivery of a rinsing liquid from a rinsing fluid tank 166 through valves 163, 164. The hydraulic control unit 161 thus controls the delivery of air or rinsing fluid to the dispensing mechanism 154 and dispensing needle cleaning mechanism 165, and controls the take up of samples or reagents by the dispensing needle.

The sensing circuit 152 and electronic control circuit 160 are connected to a data processing circuit 167 which is in turn connected to a memory circuit 168, CRT display 169, input unit 170 and data printer 171. An output signal from the sensing circuit 152 is stored in the memory circuit 168 by the data processing circuit 167, which may also cause the signal to be converted into a display on the CRT display 169, or directly into printed information by means of the printer 171. By executing a variety of computations, moreover, the data processing circuit 167 can, amongst other activities, measure the density of a variety of samples by pattern recognition or on the basis of each item of measurement data, and can print out the results on the printer 171 or permit monitoring by means of the CRT display 169. The sequence of these computations, as well as the commands sent to the electronic control circuit 160, is determined by a pre-loaded program that is started and, when necessary, modified by the input unit 170.

One example of an electrophoretic measurement employing the foregoing electronic and hydraulic circuitry will now be described. First, the buffer tanks 100 are filled with a buffer solution, reagent bottles and test tubes containing samples are set in the reagent and sample holder 90 (see FIGS. 16, 18, 19), the trays 125 with their respective covers 126 are lined up across the buffer tanks 100, and the input unit 170 enters a measurement start signal. The data processing circuit 167 responds by sending a command signal to the electronic control circuit 160 in accordance with the program loaded in the memory circuit 168, causing the positions of the trays as well as the positions of the reagent and sample holder and dispensing needle cleaning apparatus to be optically scanned for identification. If no abnormalities are detected, operation shifts to the next process step. Specifically, the dispensing needle is cleaned and then carried to a sample injection hole 137 shown in FIG. 36 to dispense a predetermined quantity of the sample, with the dispensing operation being repeated successively as required. In doing so, the optics/dispensing mechanism, dispensing needle cleaning mechanism and lifting mechanism operate as described earlier to clean the needle, take up a predetermined quantity of a sample, clean the periphery of the needle again, remove the cover from a tray, lower the dispensing needle to the prescribed position, dispense the sample, return the cover and wash the needle again, all of these steps being repeated as necessary. When the dispensing of the samples has been completed for the trays set on one pair of buffer tanks, the electrodes provided in the tanks are energized to start the electrophoretic operation, after which samples begin being applied to the next row of trays. After the passage of a predetermined period of time, the feed of electricity is cut off, a deep coloring agent is applied to the trays by the dispensing needle to color the samples, and the samples are then read to measure the density of each component.

In carrying out immunoelectrophoresis based on an immunoreaction, antiserum is dispensed into each of the antiserum grooves 138 after the electrophoretic power supply is turned off, and immunodiffusion is allowed to take place over a period of from several to several dozen hours. Sedimentation lines caused by the antigen-antibody reaction appear in the gel layer of the tray, allowing the precipitated particles to be read even without a drying treatment. The sedimentation lines permit identification of the sample components and measurement of density by means of pattern recognition. It should be noted that density measurement can be performed over a number of runs in a sequence decided by the program, and that measurements can be limited to the detection of specific components, depending upon the particular antiserum combination. Further, in order to reduce measurement errors, a standard antigen-antibody reaction can be allowed to proceed simultaneously, and a comparison can be obtained with the sedimentation line density resulting from the rate of reaction of the standard substance. Such an expedient provides greatly improved measurement accuracy.

The apparatus of the present invention, with the addition of the buffer tanks and trays, makes it possible to achieve automatic measurement with an accuracy much higher than that hitherto provided by the conventional apparatus and technique. This is attained by optically scanning the sample injection holes and antiserum injection grooves in advance to confirm their positions, dispensing the proper substances at the predetermined positions with a dimensional accuracy measured on the order of microns, measuring the positions and/or patterns of the resulting fractionated substances or of the sedimentation lines caused by an immunoreaction, with the supporting bodies remaining at rest from the beginning of the process to the end, and continuously making comparisons with previously obtained results while measurement proceed. Accordingly, much more information is obtained relating to the position, dimensions and density of reaction substances than when the systems under investigation are treated and measured independently.

The apparatus of the present invention finds use not only in the measurement of various reactions in the laboratory, but also in clinical investigations to reduce labor, provide new methods of immunological diagnosis and assist in the development thereof, and contribute to the rationalization of diagnosis and treatment.

As many apparently widely different embodiments of the present invention may be made without departing from the spirit and scope thereof, it is to be understood that the invention is not limited to the specific embodiments thereof except as defined in the appended claims.

What is claimed is:

1. An optical-type automatic analyzing and measuring apparatus which comprises an X-Y drive mechanism, and optics/dispensing mechanism having an optical system and dispensing means including a dispensing needle, a dispensing needle cleaning mechanism, a lifting mechanism having a lifter adapted to lift and lower an object remote of said dispensing needle, and a reagent/sample holder accommodating reagents and samples, wherein said optics/dispensing mechanism and said lifting mechanism are mounted on the same movable structure and transported together in two dimensions by said X-Y drive mechanism, the optical system of said optics/dispensing mechanism, the dispensing needle of said dispensing means and the lifter of said lifting mechanism are located spaced apart from one another by predetermined distances so as not to impede the operation of one another, said dispensing means is adapted to take up a predetermined quantity of a reagent or sample from said reagent/sample holder and dispense the same in prescribed quantities at each of a number of predetermined positions to allow reagents and samples to react, said optical system determines the positions of said mechanisms and said holder in a two-dimensional plane by confirming the operating position of said needle or lifting mechanism spaced apart from each other by a predetermined distance, said optical system being adapted to read the optical characteristics of a sample following a reaction with a reagent and to generate a detection signal for providing the measured results, said optical system includes a lamp housing, a light condenser, light guiding optical fibers, an irradiation lens housing, an irradiation lens, an objective lens and a light receiving element, and said rinsing needle cleaning mechanism passes a rinsing liquid and air through the interior of the dispensing needle before said needle takes up a reagent or sample, and ejects a rinsing liquid and air toward the outer surface of the dispensing needle after said needle takes up a reagent or sample, whereby the dispensing needle is rinsed and blown dry.

2. The analyzing and measuring apparatus according to claim 1, in which said dispensing needle cleaning apparatus includes a main body having a substantially conical cavity into which said dispensing needle is capable of being inserted and withdrawn, and an intermediate body disposed on said main body and over the conical cavity of said main body and having a central hole through which said dispensing needle passes and a plurality of air ejecting passages and rinsing solution ejecting passages for ejecting air and rinsing solution toward said dispensing needle when said dispensing needle is inserted into said conical cavity.

3. The analyzing and measuring apparatus according to claim 1 in which each buffer tank is provided with an electrode affixed within the interior thereof.

4. The analyzing and measuring apparatus according to claim 1, in which said X-Y drive mechanism includes an X-axis drive source for transporting the structure of said optics/dispensing mechanism and lifting mechanism along the X-axis, a Y-axis drive source for transporting the structure of said optics/dispensing mechanism and lifting mechanism along the Y-axis, a pair of X-axis guide rails, a pair of X-axis drive rollers and X-axis bushes provided on said structure for guiding said structure along said X-axis drive rails, a pair of Y-direction movement stages supporting said X-axis guide rails at both ends thereof, a pair of Y-axis guide rails, and a pair of Y-axis guide bushes provided on each of said Y-direction movement stages for guiding said stages along said Y-axis guide rails, said X-axis drive source and said Y-axis drive source each having a driving motor, a sprocket driven by said driving motor, and a slip clutch interposed between said driving motor and said sprocket.

5. The analyzing and measuring apparatus according to claim 4, in which said optics/dispensing mechanism is supported by said guide rails and said guide rollers and the dispensing means of said optics/dispensing mechanism has said dispensing needle incorporated therein and includes a needle raising and lowering mechanism for providing relative vertical movement of the dispensing needle.

6. The analyzing and measuring apparatus according to claim 1, in which said lifting mechanism includes a lifter for engaging a pair of hooks provided on a cover vertically movable above said reagent/sample holder, and a pair of buffer springs connected to said lifter.

7. The analyzing and measuring apparatus according to claim 1 or claim 6, in which said reagent/sample holder includes a holder main body, a cover attachable to said main body, and a sheet of aluminum foil interposed between said main body and said cover.

8. The analyzing and measuring apparatus according to claim 1 or claim 6, further comprising at least a pair of buffer tanks and stations for accommodating said buffer tanks.

9. The analyzing and measuring apparatus according to claim 8 in which each buffer tank is provided with an electrode affixed within the interior thereof.

10. The analyzing and measuring apparatus according to claim 1, in which a main body is provided to support said X-Y drive mechanism, said dispensing needle cleaning mechanism and said reagent/sample holder, and said X-Y drive mechanism is arranged to translate said movable structure having said optics/dispensing mechansim and lifting mechanism mounted thereon over said dispensing needle cleaning mechanism and reagent/sample holder in said two dimensions.

11. The analyzing and measuring apparatus according to claim 10, in which said optics/dispensing mechanism includes a needle raising and lowering mechanism for moving said dispensing needle toward and away from said dispensing needle cleaning mechanism and said reagent/sample holder.

12. The analyzing and measuring apparatus according to claim 10, in which said X-Y drive mechanism is arranged to bestride said dispensing needle cleaning mechanism and reagent/sample holder.

13. The analyzing and measuring apparatus according to claim 1, in which said light receiving element includes a linear image sensor having a multiplicity of photoelectric converting elements for receiving light scattered from an irradiated target surface to be scanned.

14. The analyzing and measuring apparatus according to claim 13, in which said light quiding optical fibers are arranged to irradiate light upon said target surface from a multiplicity of directions.

15. The analyzing and measuring apparatus according to claim 13, in which said light guiding optical fibers and objective lens are arranged to irradiate light in overlying rectangular shaped patterns upon said target surface.

* * * * *